US011375956B2

(12) United States Patent
Bahmanyar et al.

(10) Patent No.: US 11,375,956 B2
(45) Date of Patent: Jul. 5, 2022

(54) APPARATUS FOR SECURING A DEVICE IN A VASCULAR LUMEN

(71) Applicant: IP2IPO INNOVATIONS LIMITED, London (GB)

(72) Inventors: Mohammad Reza Bahmanyar, London (GB); Christopher Neil McLeod, London (GB)

(73) Assignee: IP2IPO INNOVATIONS LIMITED, London (GB)

(*) Notice: Subject to any disclaimer, the term of this patent is extended or adjusted under 35 U.S.C. 154(b) by 551 days.

(21) Appl. No.: 16/334,935

(22) PCT Filed: Sep. 21, 2017

(86) PCT No.: PCT/GB2017/052834
§ 371 (c)(1),
(2) Date: Mar. 20, 2019

(87) PCT Pub. No.: WO2018/055389
PCT Pub. Date: Mar. 29, 2018

(65) Prior Publication Data
US 2019/0261925 A1 Aug. 29, 2019

(30) Foreign Application Priority Data
Sep. 21, 2016 (GB) .................................... 1616092

(51) Int. Cl.
*A61B 5/00* (2006.01)
*A61B 5/0215* (2006.01)
(Continued)

(52) U.S. Cl.
CPC ............ *A61B 5/6882* (2013.01); *A61B 5/026* (2013.01); *A61B 5/0215* (2013.01);
(Continued)

(58) Field of Classification Search
CPC ... A61B 5/6882; A61B 5/6876; A61B 5/6862; A61F 2/89; A61F 2002/825;
(Continued)

(56) References Cited

U.S. PATENT DOCUMENTS 9,114,032 B1* 8/2015 Pulugurtha ............... C23F 1/44
2005/0049674 A1* 3/2005 Berra ........................ A61F 2/07
623/1.13

(Continued)

FOREIGN PATENT DOCUMENTS

EP 1068836 A2 1/2001
WO 0172240 A1 10/2001
(Continued)

OTHER PUBLICATIONS

Great Britain Examination Report for Appl No. GB1715277.8 dated Jan. 16, 2020, 4 pages.
(Continued)

*Primary Examiner* — Thomas McEvoy
(74) *Attorney, Agent, or Firm* — Maine Cernota & Rardin

(57) ABSTRACT

An implantable intravascular anchor for supporting a device inside a vascular lumen, the anchor comprising a first part configured to expand when extending from a catheter, and to collapse upon retraction into said catheter; a second part for supporting the device in the lumen and a third part, proximal to the first part, and configured so that, upon release from the catheter, it expands in width to engage an interior wall of the lumen and is adapted for securing the anchor against axial movement along the lumen.

5 Claims, 3 Drawing Sheets

(51) Int. Cl.
    *A61B 5/026*     (2006.01)
    *A61F 2/89*     (2013.01)
    *B33Y 80/00*     (2015.01)
    *A61F 2/82*     (2013.01)

(52) U.S. Cl.
    CPC .............. *A61B 5/6876* (2013.01); *A61F 2/89* (2013.01); *B33Y 80/00* (2014.12); *A61F 2002/825* (2013.01); *A61F 2220/0008* (2013.01); *A61F 2240/001* (2013.01); *A61F 2250/0002* (2013.01); *A61F 2250/0098* (2013.01)

(58) Field of Classification Search
    CPC ...... A61F 2220/0008; A61F 2250/0098; A61F 2/06; A61F 2/07
    See application file for complete search history.

(56) References Cited

U.S. PATENT DOCUMENTS

| | | |
|---|---|---|
| 2005/0154321 A1 | 7/2005 | Wolinsky et al. |
| 2006/0200030 A1 | 9/2006 | White et al. |
| 2008/0188921 A1* | 8/2008 | Yamasaki ............... A61B 5/062 623/1.13 |
| 2008/0275350 A1 | 11/2008 | Liao et al. |
| 2013/0085350 A1 | 4/2013 | Schugt |
| 2014/0275865 A1 | 9/2014 | Tammam |
| 2014/0276141 A1 | 9/2014 | Dlugach et al. |
| 2015/0150508 A1 | 6/2015 | Glenn et al. |

FOREIGN PATENT DOCUMENTS

| | | |
|---|---|---|
| WO | 20140070316 A1 | 5/2014 |
| WO | 20180055389 A3 | 3/2018 |

OTHER PUBLICATIONS

Great Britain Examination Report for Appl No. GB1715277.8 dated Mar. 28, 2019, 6 pages.
Great Britain Examination Report for Appl No. GB1715277.8 dated Aug. 30, 2019, 7 pages.
PCT Written Opinion for Appl No. PCT/GB2017/052834 dated Jan. 9, 2018, 9 pages.

* cited by examiner

APPARATUS FOR SECURING A DEVICE IN A VASCULAR LUMEN

RELATED APPLICATIONS

This application is a national phase application filed under 35 USC § 371 of PCT Application No. PCT/GB2017/052834 with an International filing date of Sep. 21, 2017 which claims priority of GB Patent Application 1616092.1 filed Sep. 21, 2016. Each of these applications is herein incorporated by reference in their entirety for all purposes. This application is related to PCT Application No. PCT/GB2017/052801 with an International filing date of Sep. 20, 2017 which claims priority of GB Patent Application 1616096.2 filed Sep. 21, 2016; PCT Application No. PCT/GB2017/052802 with an International filing date of Sep. 20, 2017 which claims priority of GB Patent Application 1616090.5 filed Sep. 21, 2016; PCT Application No. PCT/GB2017/052804 with an International filing date of Sep. 20, 2017 which claims priority of GB Patent Application 1616091.3 filed Sep. 21, 2016; and PCT Application No. PCT/GB2017/053313 with an International filing date of Nov. 2, 2017 which claims priority of GB Patent Application 1618508.4 filed Nov. 2, 2016; each of these applications is herein incorporated by reference in their entirety for all purposes.

FIELD

This invention relates to implantable intravascular devices. More specifically, the invention provides an apparatus for supporting a device in a vascular lumen. In particular, the invention relates to a catheter-deployable apparatus arranged to be deployed in a vascular lumen, such as a human artery.

BACKGROUND

It may be desirable to position a device, such as a telemetric sensor device, in a human artery, such as the pulmonary artery for example, in order to measure certain parameters, such as blood flow rate or pressure, for example. When positioning a device in the pulmonary artery it may be important to ensure that it is correctly orientated, against an anterior wall of the artery for example. It may also be important to ensure that the device is fixed securely in place within the artery because detachment of the device from the artery may cause it to cause obstruction and/or damage to the surrounding tissue and maybe even to the heart itself, causing death in the worst instance.

SUMMARY

Aspects and embodiments of the present disclosure aim to address at least some of these issues. Aspects and embodiments of the present disclosure are set out in the appended claims. These and other aspects and embodiments are also described herein.

Described herein is an implantable intravascular anchor for supporting a device inside a vascular lumen, the anchor comprising: first part configured to expand when extending from a catheter, and to collapse upon retraction into said catheter; a second part for supporting the device in the lumen; and a third part, proximal to the first part, and configured so that, upon release from the catheter, it expands in width to engage an interior wall of the lumen and is adapted for securing the anchor against axial movement along the lumen.

Optionally, the first part and the third part may comprise resilient material. Optionally, the apparatus may be arranged to position the device towards the interior wall of the lumen. Optionally, the first part may be arranged to contact at least part of the interior wall on an opposite side of the lumen from the device. Optionally, the third part may be configured to hold the anchor in alignment with the lumen, for example aligned along the lumen. Optionally, the third part may be arranged to form, when expanded, a circumferential band at least partially inscribing the interior wall of the lumen. Optionally, the third part may comprise a plurality of struts at least partially aligned with the lumen, for example wherein the band is provided by a meandering pattern comprising the struts. Optionally, the second part may be disposed between the first part and the third part.

The apparatus may further comprise the device, for example wherein the device is coupled to the second part in a fixed orientation.

Optionally, the first part and the third part may be arranged so that, when in use, the third part is expanded into engagement with the interior wall of the lumen, and a major dimension, optionally the largest dimension, of the device is aligned with the lumen. Optionally, the first part may comprise a loop, for example a tear-drop shaped loop.

Optionally, the first part may comprise an elongate member that, when extending from the catheter, partially unbends into a nonplanar shape, for example a non-flat shape, for example wherein the elongate member defines at least part of a boundary of said non-flat shape.

Optionally, the apparatus may further comprise at least one radio opaque marker arranged to indicate the rotational orientation of the anchor about its axis in a two-dimensional, 2D, radiography image of the anchor in plan. Optionally, the first part may carry the radio opaque marker. Optionally, the at least one radio opaque marker may be positioned toward an end of the first part opposite the second part, for example about a distal tip of the first part.

Optionally, the at least one radio opaque marker may comprise at least three discrete radio opaque markers. Optionally, the at least one radio opaque marker may comprise an elongate radio opaque marker. Optionally, the at least one marker may be distributed about the end of the first part, for example wherein it is asymmetric about the end.

Also described herein is an apparatus for orientating an implantable intravascular device inside a vascular lumen, comprising: a first part configured to expand upon release from a catheter and to collapse upon retraction into said catheter; a second part adapted to support the device in the lumen; and at least one radio-opaque marker provided on the first part; wherein said at least one marker is arranged on said first part to indicate the rotational orientation of the apparatus about its axis in a two-dimensional, 2D, radiography image of the apparatus in plan.

Optionally, a plurality of radio-opaque markers may be provided on the first part, said markers being provided in a spaced-apart arrangement. Optionally, at least three discrete radio-opaque markers may be provided on the first part, said markers being arranged towards a distal end of the first part. Optionally, the first part, may be formed as a loop, for example a tear-drop shaped loop, preferably wherein a first radio-opaque marker is positioned toward the distal end of the loop, for example at the tip, and second and third radio-opaque markers are arranged along opposing sides of the loop separated by the first radio-opaque marker.

Optionally, the loop may be arranged to extend away from the mounting at a deflected angle, for example wherein the loop is arranged at an angle greater than zero from a plane of the second part, for example an angle greater than about 15 degrees. Optionally, the apparatus comprises a third part, proximal to the first part, and configured so that, upon release from the catheter, it expands in width, for example radially, to engage an interior wall of the lumen, optionally wherein the third part is adapted for securing the apparatus against axial movement along the lumen.

Optionally, the third part (of any aspect described herein) is configured to have a meandering configuration for expanding against an interior wall of the lumen. Optionally, on any of the apparatuses described herein, a further radio opaque marker is provided at an end of the third part opposite from the first part. Optionally, at least one of the first part and third part comprises nitinol wire. Optionally, at least one of the first part and third part comprises a bio-absorbable material. Preferably, the apparatus is totally absorbable by the tissue of the lumen such that only the endothelialised device remains. Other suitable materials include polymers and metals.

Also described herein is a system for intravascular implantation of a device, comprising a catheter and an apparatus as described herein.

Optionally, the anchor may be arranged in the catheter so that the first part is nearer to a deployment opening of the catheter than the third part.

Also described herein is a method of deploying an anchor in a vascular lumen, comprising: partially deploying a first part of an anchor from a catheter in a vascular lumen, wherein the first part is configured to expand as it is deployed; identifying, based on a two dimensional image of the expanded first part in the lumen, at least one of: (i) a roll angle of the anchor about a longitudinal axis of the lumen; and (ii) a longitudinal position of the anchor along the lumen; at least partially undeploying the first part of the anchor to collapse it back into the catheter; adjusting the roll angle based on said identifying; and deploying the anchor into the lumen for positioning a device in the lumen.

Optionally, the first part of the anchor may carry a radio opaque orientation marker. The anchor may carry the device at a fixed roll position, and adjusting the roll angle of the anchor fixes the roll orientation of the device in said lumen. Optionally, deploying the anchor into the lumen for positioning a device in the lumen may comprise irreversibly releasing a third part of the anchor from the catheter for securing the device against movement along the lumen. Alternatively, the third part of the anchor may be retractable into the catheter after deployment, preferably to allow the anchor to be withdrawn or realigned, even after full deployment. For example, a "thread" may run through at least part of the third part to allow it to be collapsed, preferably remotely.

Optionally, adjusting the roll angle may comprise selecting the position of a second part of the anchor when deployed.

Optionally, the anchor may be rotated to adjust the roll angle during imaging of the first part using a radiography technique to perform said identifying. Optionally, the imaging may collect two-dimensional, 2D, images aligned with the lumen. Optionally, the anchor may comprise an anchor or apparatus as described herein.

Optionally, the first part may be formed as a loop, and the method may further comprise: allowing the three markers to spread out during partial deployment of the loop from the catheter; and rotating the loop to determine its rotational alignment in the lumen; wherein the rotational alignment of the loop is determined by monitoring, using a radiography technique, for an increase or decrease in the spacing between a first centrally-located marker and at least one or both of the two further markers provided on opposing sides of the loop as it is rotated.

Optionally, the anchor may comprise a third part having provided thereon a further radio opaque marker, and the method may further comprise: determining the position of the further radio opaque marker in the lumen prior to deploying the third part to ensure that the anchor is correctly positioned, for example to ensure that it is downstream of a valve in the lumen.

Optionally, the lumen is a human pulmonary artery, and the anchor may be arranged to position the device adjacent the anterior wall of said artery.

Also described herein is a machine-readable map, or machine-readable instructions, configured to enable a 3D printer (or any printer or manufacturing device/system) to manufacture at least part of an apparatus as herein described.

As used herein, the term "apparatus" preferably connotes an anchor or device as described herein. As used herein, means plus function features may be expressed alternatively in terms of their corresponding structure.

BRIEF DESCRIPTION OF THE DRAWINGS

Aspects and embodiments will now be described, by way of example only, with reference to the accompanying drawings, in which.

DETAILED DESCRIPTION

Figure 1:
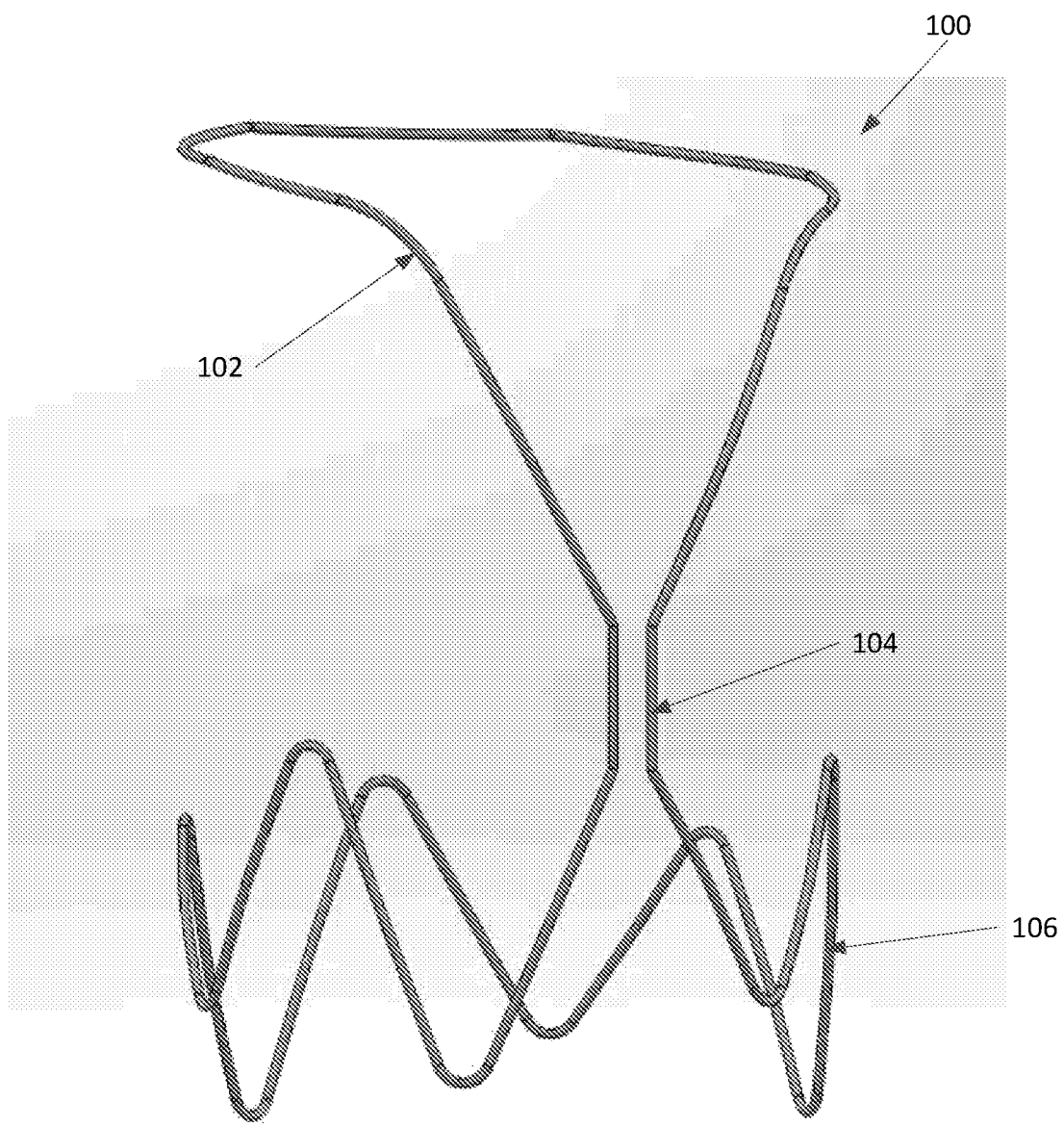
FIG. 1 shows an implantable intravascular anchor.
Figure 2:
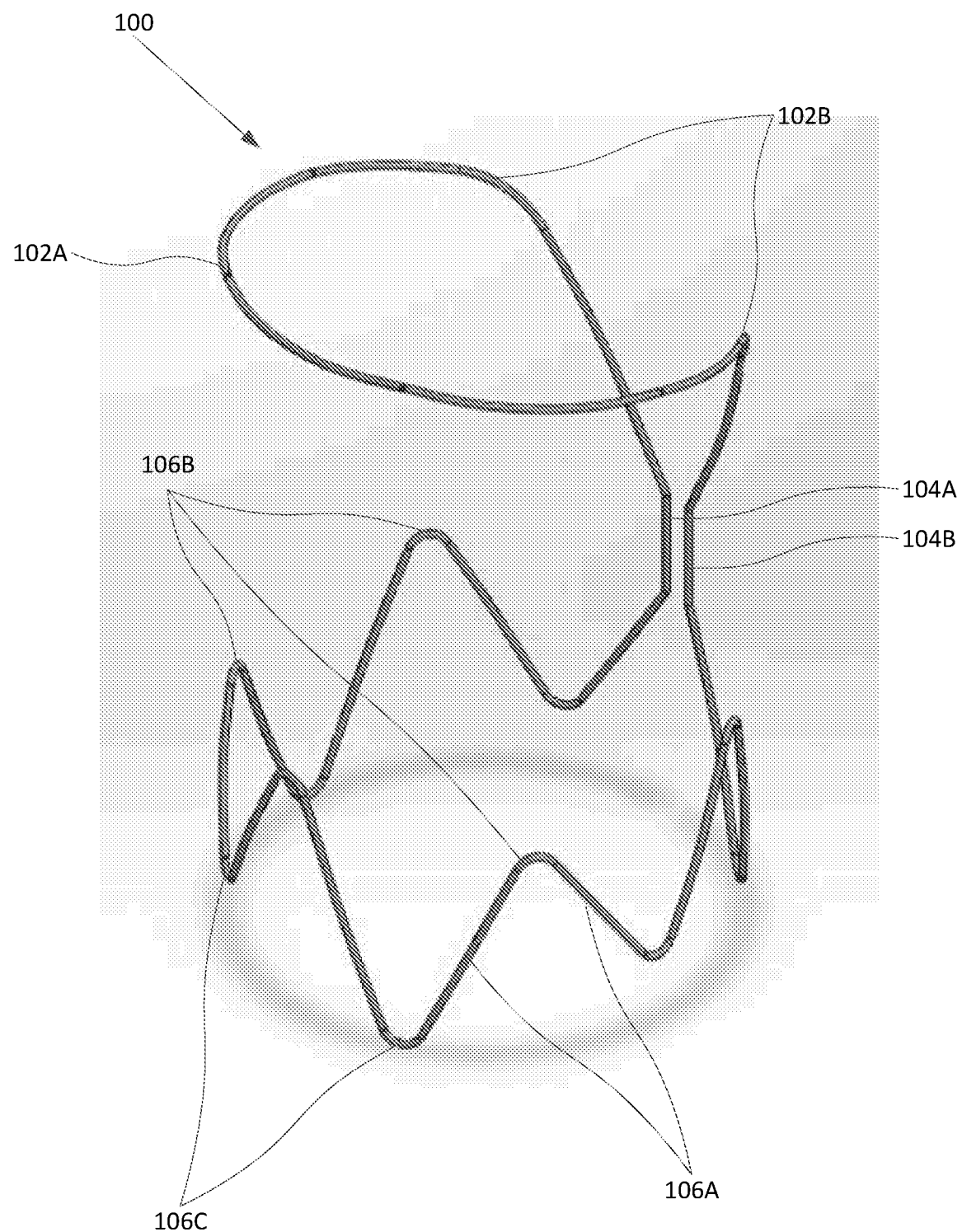
FIG. 2 shows a different view of the implantable intravascular anchor.

An implantable intravascular anchor 100 according to an exemplary embodiment of the present invention is shown in FIGS. 1 and 2. The anchor 100 is arranged to be implanted in a vascular lumen, preferably an artery such as the human pulmonary artery. Accordingly, the anchor 100 is arranged to be implanted in a lumen, which are typically considered to be generally cylindrical or tubular in shape, such that it extends in an axial direction along the lumen.

FIG. 1 shows the exemplary anchor 100 is formed of three parts: a first part 102, a second part 104 and a third part 106. The second part 104 extends between the first and third parts 102, 106, thereby connecting them. The first and third parts 102, 106 are configured to fix the anchor 100 in a lumen in an axial direction. The second part 104 is arranged to support (or carry) a device (for example, a telemetric sensor device) in the lumen.

At least the first and third parts 102, 106 are formed of a resilient material that allows them to be compressed such that the anchor 100 can fit within a delivery device, such as the lumen of a catheter, and expand in width when released. The first and third parts 102, 106 have a width that, when released to expand within a lumen such as an artery, causes the first and third parts 102, 106 to engage an interior wall of the artery.

The first part 102 is arranged to bias the second part 104 of the anchor 100 towards an interior wall of the lumen, for example the anterior wall of the pulmonary artery, as will now be discussed in more detail.

Referring now both to FIGS. 1 and 2, the first part 102 is at least in part arranged to form a loop 102A. The loop 102A is deflected (for example, bent) at points 102B, away from the 'axial' plane of the second part 104, which is arranged to be orientated in a generally axial direction within a lumen. In other words, the first part 102 may, at least in part, adopt a non-planar (e.g. a non-flat) shape when released from a deployment catheter. The loop 102A is, preferably, generally tear-drop shaped, for example if the first part 102 is considered from a perspective view in which it appears to be planar (or prior to the loop 102A being 'deflected'). The first part 102 may therefore be considered to have, at least in part, an elongate member, which may define at least part of a boundary of the non-planar shape.

The second part 104 consists essentially of two parallel struts 104A, 104B, which are axially aligned and arranged to support a device (not shown). The struts 104A, 104B may be formed as an integral part of the anchor 100, and threaded through the device to secure it. The device may be formed onto the struts, for example it may be clamped or 'welded' (e.g. soldered) onto the struts 104A, 104B, and may comprise quartz crystal, for example. The open ends of the anchor 100 may be welded to form a closed structure, before securing the device to the struts 104A, 104B by soldering or adhesive. Alternatively, the device may be secured by introducing kinks (not shown) on the struts 104A, 104B close to the device. The radial extent of the second part may be less than that of the first part and the third part. It may also be off centre—i.e. towards a radially outer position.

The anchor 100 is arranged to support and/or carry a device (not shown) on the second part 104 such that, when the anchor 100 is implanted in a lumen, the device is positioned towards the interior wall of the lumen. To achieve this, the deflected loop 102A, and preferably an extremity (or distal part) of the deflected loop 102A, can be orientated within a lumen to contact at least part of generally opposing portion of the interior wall of the lumen to that which the second part 104 is to be positioned. As such, the deflection may be between about 15 degrees and about 90 degrees, depending on the overall length of the anchor 100 and/or dimensions of the lumen for which it is intended.

In a preferred configuration, the anchor 100 may be orientated such that the second part 104 (and hence the device) is positioned against an anterior wall of a human pulmonary artery. Ideally, the device may be positioned against the interior wall of a lumen so that it engages the interior wall. In such a configuration, the first part 102 may be arranged to contact the posterior wall of the human pulmonary artery.

The third part 106 is arranged to engage the interior wall of an artery (or other lumen) and thereby hold the anchor 100 in place. The third part 106, preferably, secures the anchor 100 against axial movement along (i.e. within) the lumen. In the embodiment shown, the third part 106 is arranged to hold the anchor 100 in alignment with the lumen, for example aligned along the lumen, preferably in an axial (i.e. longitudinal) orientation. As such, a major dimension of the anchor 100 is aligned with the lumen, preferably in an axial direction, for example in the direction of flow through the lumen.

The third part 106, when expanded, is arranged to form a circumferential band, which at least partially inscribes the interior wall of the lumen, once implanted. In the embodiment shown, the third part 106 is formed by a plurality of struts 106A. The struts 106A are, preferably, arranged to at least partially align with an interior wall of the lumen, once the anchor 100 is implanted. The struts 106A form a band having a meandering pattern (i.e. bending back and forth) with a plurality of peaks 106A and a plurality of troughs 106B. The band is configured in a generally circular/circumferential arrangement so as to conform to the interior wall of a lumen. For example they may be arranged in a concertina type arrangement so that compressing the third part radially causes the struts to align axially with each other. Whereas as the third part is expanded radially, the peaks and troughs unbend and the struts become progressively less axially aligned. In this way, the anchor 100 should cause minimal obstruction to flow of liquid (e.g. blood) through the lumen.

The anchor is configured to be arranged in a catheter (not shown) for deployment such that the first part 102 is ahead of the third part 106 with respect to a deployment opening of the catheter. In other words, the anchor 100 is arranged such that during deployment, the first part 102 is released first.

Figure 3:
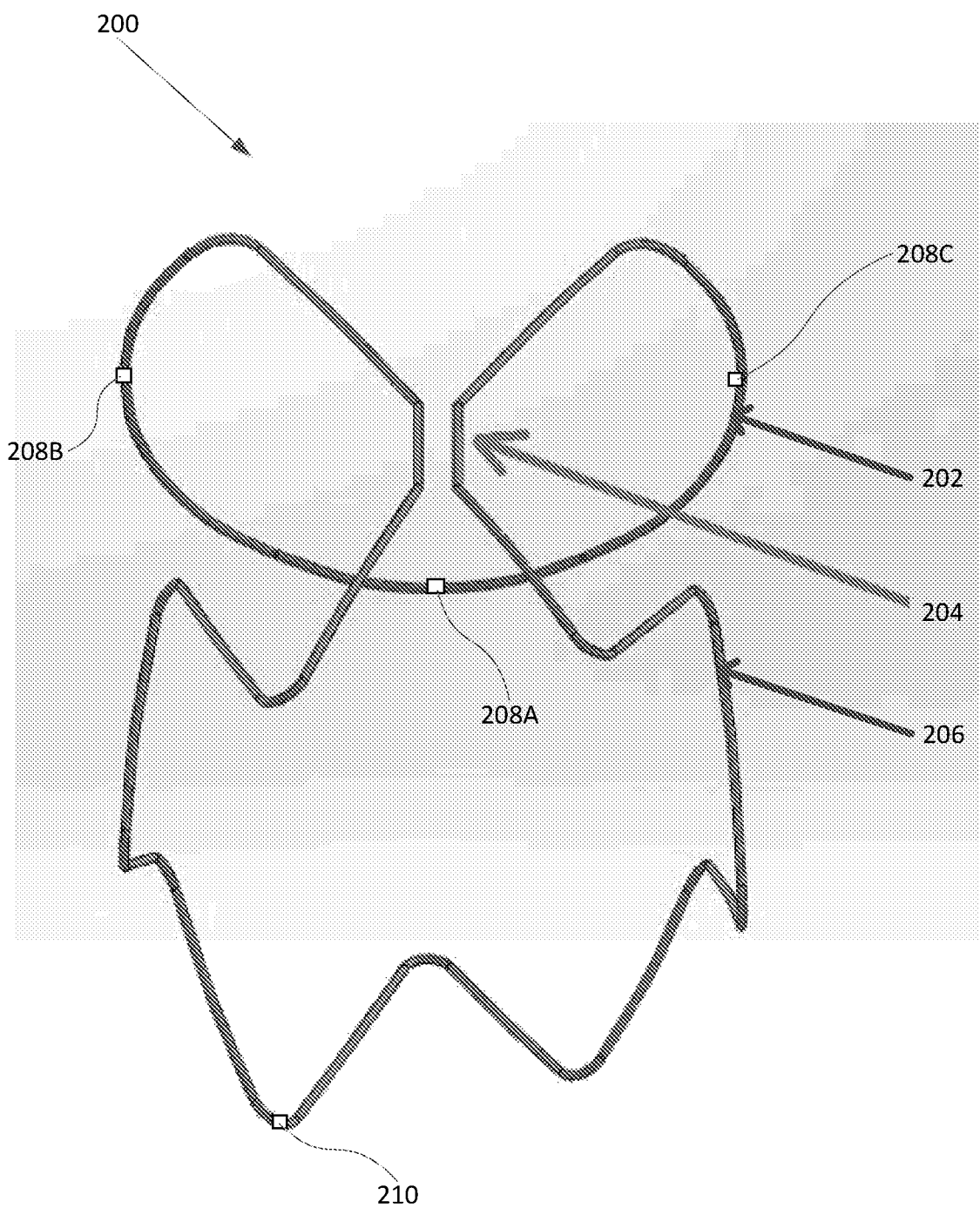
FIG. 3 shows an implantable intravascular anchor having radiopaque markers.

FIG. 3 shows an anchor 200 that is structurally similar to the anchor 100 previously described. However, this anchor 200 has a plurality of radiopaque markers 208A, 208B, 208C, 210 arranged on the anchor 200 at various locations, which may be used to indicate the rotational orientation of the anchor 200 in, for example, a two-dimensional (2D) radiography image. The arrangement of markers 208A, 208B, 208C on the first part 202 of the anchor 200 can help to orientate it correctly within a lumen, for example such that a device supported by a second part 204 of the anchor 200 is positioned against an interior wall of the lumen. The marker 210 provided on the third part 206 of the anchor 200 can be used to indicate that the anchor 200 has been fully deployed from a deployment catheter (not shown). As such, the marker 210 on the third part 206 should, ideally, be located on a distal extremity of the anchor 200, as shown in FIG. 3. Of course, additional anchors may be provided for additional sensitivity and/or accuracy of measurements.

At least one radiopaque marker is required on the first part 202 to indicate the orientation of the anchor in a lumen. On the anchor 200 shown, three markers 208A, 208B, 208C are provided, with a first marker 208A being located on a distal tip of the first part 202 (i.e. towards an end of the first part 202), which is generally opposite the second part 204. Second and third markers 208B, 208C are located along opposing sides of the first part 202, preferably such that they oppose one another. Alternatively, a marker (not shown) may have an elongate configuration, preferably distributed about the end of the first part 202, for example wherein the marker is asymmetric about the end.

The anchor 100, 200 may be implanted into a lumen (not shown) as follows. The first part 102, 202 is partially deployed from a catheter into the lumen, wherein the first part is configured to expand as it is deployed. A two-dimensional (2D) image of the expanded first part 102, 202 in the lumen is then used to identify at least one of: a roll angle of the anchor about a longitudinal axis of the lumen; and a longitudinal position of the anchor along the lumen. If it is determined that the first part 102, 202 is not correctly orientated in the lumen, it can be at least partially undeployed to collapse it back into the catheter.

The roll angle of the anchor 100, 200 can then be adjusted based on the previous identification step, and the anchor 100, 200 can then be redeployed into the lumen, whereby to position a device (not shown) that is supported or carried by the second part 104, 204 of the anchor 100, 200 in the lumen.

When adjusting the roll angle, the position of the second part 104, 204 of the anchor 100, 200 when deployed may be selected. A radiography technique may be used to rotate the anchor 100, 200 to adjust the roll angle during imaging of the first part 102, 202, preferably wherein two-dimensional (2D) images of the anchor 100, 200 aligned with the lumen are obtained and/or used.

If an anchor 200 having a 'loop' shaped first part 202 and three radiopaque markers 208A, 208B, 208C is used, such as the anchor 200 described with reference to FIG. 3, the three markers 208A, 208B, 208C can be allowed to spread out during partial deployment of the first part 202 from the catheter, and, if required, the first part 202 can be rotated to determine its rotational alignment in the lumen. The rotational alignment of the first part 202 can then be determined by monitoring using a radiography technique, for example, for an increase or decrease in the spacing between the first centrally-located marker 208A and at least one or both of the two further markers 208B, 208C provided on opposing sides of the first part 202 as it is rotated. The increase or decrease in spacing between the first marker 308A and the second and/or third markers 208B, 208C can be used to indicate the direction of rotation and hence the orientation of the anchor 200 inside the lumen.

If a further radiopaque marker 210 is provided on the third part 206, the position of the further radiopaque marker 210 in the lumen may be determined prior to deploying the third part 206 to ensure that the anchor 200 is correctly positioned, for example to ensure that it is downstream of a valve (not shown) in the lumen.

In one embodiment of the anchor 100, 200, release of the third part 106, 206 of the anchor 100, 200 to secure the device against (preferably axial) movement along the lumen may be irreversible, due to the third part 106, 206 being configured such that it cannot be retracted into the catheter once deployed, for example if it has fully expanded.

However, in another embodiment (not shown) the third part 106, 206 may be configured such that it can be undeployed (i.e. retracted) into the catheter so that the anchor 100, 200 can be withdrawn or realigned, as required. For example, a thread may pass through one or more of the struts of the third part 206, which can be used to compress (for example, drawing or pulling) the struts together to enable the retraction. This is, of course, simply an example of how the third part 106, 206 may be configured to be retractable.

In the examples shown, the anchor 100, 200 is formed of wire, such as nitinol wire, though other materials may be used. Ideally, the anchor 100, 200 may be formed of a bio-absorbable material which allows it to be absorbed into the tissue of a human body when deployed in an artery, for example, preferably leaving an endothelialised device on the wall of the artery behind once the anchor 100, 200 has been substantially absorbed.

In one example, the device may comprise quartz crystal having channels through which the struts 104A, 104B are passed. The struts 104A, 104B can then be heated so that they bond by solder to a metallic film deposited within the channels of the quartz. The whole anchor 100 may be formed from a single piece of nitinol wire, such that one channel contains a single strut and the other channel contains the two ends of the anchor so that, when soldered, there is one continuous loop portion. This arrangement may strengthen the joint in the nitinol to improve its resistance to fatigue.

As briefly mentioned, the anchor described herein may optionally be manufactured by way of '3D printing' whereby a three-dimensional model is supplied, in machine-readable form, to a '3D printer' adapted to manufacture said anchor. This may be by additive means such as extrusion deposition, Electron Beam Freeform Fabrication (EBF), granular materials binding, lamination, photopolymerization, or stereolithography or a combination thereof. The machine-readable model comprises a spatial map of the object or pattern to be printed, typically in the form of a Cartesian coordinate system defining the object's or pattern's surfaces. This spatial map may comprise a computer file which may be provided in any one of a number of file conventions. One example of a file convention is a STL (STereoLithography) file, which may be in the form of ASCII (American Standard Code for Information Interchange) or binary, and which specifies areas by way of triangulated surfaces with defined normals and vertices.

An alternative file format is AMF (Additive Manufacturing File) which provides the facility to specify the material and texture of each surface of the anchor as well as allowing for curved triangulated surfaces. The mapping of the anchor may then be converted into instructions to be executed by 3D printer according to the printing method being used. This may comprise splitting the model into slices (for example, each slice corresponding to an x-y plane, with successive layers building the z dimension) and encoding each slice into a series of instructions. The instructions sent to the 3D printer may comprise Numerical Control (NC) or Computer NC (CNC) instructions, preferably in the form of G-code (also called RS-274), which comprises a series of instructions regarding how the 3D printer should act. The instructions vary depending on the type of 3D printer being used, but in the example of a moving printhead the instructions include: how the print-head should move, when/where to deposit material, the type of material to be deposited, and the flow rate of the deposited material.

Any part of the apparatus described herein may be embodied in one such machine-readable model, for example a machine-readable map or instructions, for example to enable a physical representation of said part of the apparatus to be produced by 3D printing. This may be in the form of a software code mapping of one or more components and/or instructions to be supplied to a 3D printer (for example numerical code).

The above embodiments are to be understood as illustrative examples. Further embodiments are envisaged. For example the device may be attached to the second part so that when the anchor is deployed into the lumen (e.g. when the first part and the third part are expanded into engagement with the interior wall of the lumen) the device carried on the second part of the anchor is disposed nearer to a wall of the vascular lumen than to its centre. For example it may hold the device against the wall of the lumen.

The device may comprise an intravascular pressure sensor for sensing fluid pressure in the lumen. The device may comprise a sensing surface disposed on a surface of the device for sensing intravascular pressure. The device may be fixed to the anchor so that when the anchor is deployed in the lumen, the sensing surface is directed away (e.g. faces away) from the adjacent wall of the lumen. For example the sensing surface may face radially inward toward the interior of the lumen face towards the centre of the lumen or an opposite wall of the lumen.

It will be appreciated that a wide variety of configurations may be adopted. For example as noted above, the device may be coupled to the anchor (e.g. to the second part) in a fixed orientation. As also noted above, third part is adapted for securing the anchor against axial movement along the lumen. Optionally, the first part and the third part may be arranged so that, when in use, the third part is expanded into engagement with the interior wall of the lumen, and a major dimension, optionally the largest dimension, of the device is aligned with the lumen. The first part may comprise a loop, for example a tear-drop shaped loop.

The asymmetry of the devices illustrated in the drawings may assist deployment of the anchor into a lumen. For example it may provide the ability to deploy the first part from the end of a catheter, check the orientation of the anchor (e.g. using radiography techniques) and then recollapse it by retracting it into the catheter. Once the correct orientation has been identified, the anchor can be fully deployed so that the third part can engage with the lumen to secure the anchor against axial movement along the lumen. It will however be appreciated in the context of the present disclosure that such asymmetry is optional. The anchor may be at least partially symmetric in the sense that the first part and the third part may have a similar configuration. For example, the first part and the third part may be symmetric about the second part—at least in terms of their function and geometry. The precise dimensions of course need not be symmetric. For example, like the third part, the first part may be adapted for securing the anchor against axial movement along the lumen.

The first part typically comprises a loop, such as a teardrop shaped loop. This loop may be provided by an elongate member, such as nitinol wire, that returns to a pre-formed shape when it is released from tension or compression e.g. when it is deployed from a catheter. Such a loop may partially unbend into a nonplanar shape, for example a non-flat shape. For example the elongate member may define at least part of a boundary of said non-flat shape. As a result, when it is deployed, the loop provided by the first part may extend axially along the lumen but also may extend across the axis of the lumen—for example the ends and/or sides of the loop may engage with different sides of the lumen. This may inhibit slippage of the first part and may act to hold the device in a selected position in the lumen.

It is to be understood that any feature described in relation to any one embodiment may be used alone, or in combination with other features described, and may also be used in combination with one or more features of any other of the embodiments, or any combination of any other of the embodiments. Any apparatus feature as described herein may also be provided as a method feature, and vice versa. Furthermore, equivalents and modifications not described above may also be employed without departing from the scope of the invention, which is defined in the accompanying claims.

What is claimed is:

1. A method comprising:
    partially deploying a first part of an anchor from a catheter in a vascular lumen, wherein the first part is a loop and is configured to expand as it is deployed;
    identifying, based on a two dimensional image of the expanded first part in the lumen, at least one of:
        (i) a roll angle of the anchor about a longitudinal axis of the lumen; and
        (ii) a longitudinal position of the anchor along the lumen;
    at least partially undeploying the first part of the anchor to collapse it back into the catheter;
    adjusting the roll angle based on said identifying to select the position of a second part of the anchor such that a device supported by the second part of the anchor is positioned against an interior wall of the lumen when the anchor is deployed; and
    deploying the anchor into the lumen for positioning a device in the lumen;
    wherein identifying comprises:
        allowing three radio opaque orientation markers carried on the first part to spread out during partial deployment of the loop from the catheter; and
        rotating the loop to determine its rotational alignment in the lumen;
    wherein the rotational alignment of the loop is determined by monitoring, using a radiography technique, for an increase or decrease in the spacing between a first centrally-located marker of the three markers and at least one or both of the two further markers provided on opposing sides of the loop as it is rotated.

2. The method of claim 1, wherein the anchor carries the device at a fixed roll position, and adjusting the roll angle of the anchor fixes the roll orientation of the device in said lumen.

3. The method of claim 1, wherein deploying the anchor into the lumen for positioning the device in the lumen comprises irreversibly releasing a third part of the anchor from the catheter for securing the device against movement along the lumen.

4. The method of claim 1, wherein the anchor comprises a third part having provided thereon a further radio opaque marker, the method further comprising:
    determining the position of the further radio opaque marker in the lumen prior to deploying the third part to ensure that the anchor is correctly positioned, for example to ensure that it is downstream of a valve in the lumen.

5. The method of claim 1 further comprising:
    manufacturing at least part of the anchor, by machine-readable instructions configured to enable a 3D printer to manufacture at least part of the anchor.

* * * * *